US009490662B2

(12) United States Patent
Shinohara

(10) Patent No.: US 9,490,662 B2
(45) Date of Patent: Nov. 8, 2016

(54) POWER SUPPLY SWITCHING CIRCUIT AND ARTIFICIAL HEART SYSTEM

(71) Applicant: SUN MEDICAL TECHNOLOGY RESEARCH CORPORATION, Suwa-shi, Nagano (JP)

(72) Inventor: Kazuto Shinohara, Suwa (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 0 days.

(21) Appl. No.: 14/436,481

(22) PCT Filed: Sep. 30, 2013

(86) PCT No.: PCT/JP2013/076621
§ 371 (c)(1),
(2) Date: Apr. 17, 2015

(87) PCT Pub. No.: WO2014/061436
PCT Pub. Date: Apr. 24, 2014

(65) Prior Publication Data
US 2015/0249365 A1    Sep. 3, 2015

(30) Foreign Application Priority Data

Oct. 19, 2012  (JP) .................................. 2012-232430

(51) Int. Cl.
*B23K 11/24*    (2006.01)
*H02J 9/06*    (2006.01)
(Continued)

(52) U.S. Cl.
CPC .................. *H02J 9/061* (2013.01); *A61M 1/10* (2013.01); *A61M 1/127* (2013.01); *H02J 7/008* (2013.01);
(Continued)

(58) Field of Classification Search
CPC ...................................................... H02J 9/061
See application file for complete search history.

(56) References Cited

U.S. PATENT DOCUMENTS

| 5,945,816 A | 8/1999 | Marusik |
| 6,545,445 B1 | 4/2003 | McDermott et al. |

(Continued)

FOREIGN PATENT DOCUMENTS

| JP | 58-136352 A | 8/1983 |
| JP | 9-19085 A | 1/1997 |

(Continued)

OTHER PUBLICATIONS

Wei Wang: "Power Module with Series—connected MOSFETs in Flip-chip Configuration", submitted to the Faculty of the Virginia Polytechnic Institute and State University in partial fulfillment of the requirements for the degree of Master of Science in Electrical Engineering, Aug. 23, 2010.

(Continued)

*Primary Examiner* — Daniel Cavallari
(74) *Attorney, Agent, or Firm* — Hauptman Ham, LLP

(57) ABSTRACT

A power source switching circuit for selectively connecting first and second power sources, at least one of which is a battery power source, to a load includes first and second power source connection parts for connection to the first and second power sources, a load connection part for connection to the load, first and second switch parts between each power source connection part and the load connection part, and a switching control part configured to perform a switch control of each switch part. Each switch part includes a plurality of FETs serially connected in the same direction such that a cathode side of a body diode is arranged on a load connection part side. The number of FETs is such that a sum of forward drop voltages of the body diodes exceeds the difference between a full charge voltage and a discharge voltage of the battery power source.

10 Claims, 11 Drawing Sheets

(51) Int. Cl.
*A61M 1/12* (2006.01)
*H02J 7/00* (2006.01)
*H03K 17/30* (2006.01)
*A61M 1/10* (2006.01)

(52) U.S. Cl.
CPC ............... *H02J 7/0068* (2013.01); *H02J 9/06* (2013.01); *H03K 17/302* (2013.01); *A61M 2205/16* (2013.01); *H02J 2009/068* (2013.01); *H03K 2017/307* (2013.01); *Y10T 307/625* (2015.04)

(56) References Cited

U.S. PATENT DOCUMENTS

| | | | | |
|---|---|---|---|---|
| 7,893,560 | B2 * | 2/2011 | Carter | H02J 1/10 307/64 |
| 8,278,888 | B2 * | 10/2012 | Egan | G05F 1/563 323/266 |
| 8,853,885 | B2 * | 10/2014 | Umminger | H02J 1/10 307/112 |
| 2002/0039034 | A1 | 4/2002 | Kohda | |
| 2006/0050460 | A1 | 3/2006 | Ebata | |
| 2010/0231048 | A1 | 9/2010 | Chen et al. | |

FOREIGN PATENT DOCUMENTS

| | | |
|---|---|---|
| JP | 10-320081 A | 12/1998 |
| JP | 10-336912 A | 12/1998 |
| JP | 11-215737 A | 8/1999 |
| JP | 2002-112469 A | 4/2002 |
| JP | 2003-533159 A | 11/2003 |
| JP | 2004-302665 A | 10/2004 |
| JP | 2006-101684 A | 4/2006 |
| JP | 2008-86100 A | 4/2008 |
| JP | 2008-99404 A | 4/2008 |
| JP | 2012-5208 A | 1/2012 |
| JP | 2012-5287 A | 1/2012 |

OTHER PUBLICATIONS

Extended European Search Report dated Aug. 7, 2015, corresponding to European Patent Application No. 13847151.1.
International Search Report mailed Oct. 29, 2013 in International Application No. PCT/JP2013/076621.

* cited by examiner

| | p1 | p2 | p3 |
|---|---|---|---|
| $Vin \geq V1$ | L | L | L |
| $V1 > Vin \geq V2$ | H | L | L |
| $V2 > Vin \geq V3$ | H | H | L |
| $V3 > Vin \geq 0$ | H | H | H |

FIG.6

| FIRST POWER SOURCE CONNECTOR | SECOND POWER SOURCE CONNECTOR | DISPLAY EXAMPLE | |
|---|---|---|---|
| BATTERY (100%) | NOT CONNECTED | 🔋(full) | |
| BATTERY (APPROXIMATELY 60%) | NOT CONNECTED | 🔋(60%) | |
| NOT CONNECTED | BATTERY (100%) | | 🔋(full) |
| BATTERY (100%) | BATTERY (100%) | ▌▌▌ | 🔋(full) |
| BATTERY (APPROXIMATELY 30%) | BATTERY (100%) | 🔋(30%) | ▌▌▌ |
| NOT CONNECTED | AC/DC POWER SOURCE | | 🔌 |
| BATTERY (LESS THAN 60%) | AC/DC POWER SOURCE | ▌▌ | 🔌 |
| AC/DC POWER SOURCE | BATTERY (LESS THAN 30%) | 🔌 | ▌ |
| AC/DC POWER SOURCE | AC/DC POWER SOURCE | 🔌 | 🔌 |

FIG.10

POWER SUPPLY SWITCHING CIRCUIT AND ARTIFICIAL HEART SYSTEM

RELATED APPLICATIONS

The present application is a National Phase of International Application Number PCT/JP2013/076621, filed Sep. 30, 2013, which claims priority to Japanese Application Number 2012-232430, filed Oct. 19, 2012.

TECHNICAL FIELD

The present invention relates to a power source switching circuit, an artificial heart system and the like.

BACKGROUND ART

Conventionally, to continuously supply a power source to a load such as electric equipment typified by an artificial heart system or the like, a plurality of power sources are connected to a power source switching circuit, and the power source switching circuit is configured to select one power source. The power source switching circuit of this type includes, for example, a field effect transistor (hereinafter referred to as "FET") which constitutes an electronic switch. The power source switching circuit switches a supply source of power source by controlling turning on or off of the FET using a logic circuit or a microcomputer. Techniques relating to such a power source switching circuit are disclosed in patent document 1 to patent document 5, for example.

Patent document 1 discloses the technique where an erroneous operation of a PMOS transistor can be prevented in a backup operation by preventing the generation of a potential difference between a gate voltage and a source voltage of the PMOS transistor connected between a main power source and a sub power source. Patent document 2 discloses the technique where at the time of switching from one power source to the other power source, an output of one power source is stopped in response to an output of the other power source thus preventing an instantaneous drop of a supply voltage. Patent document 3 discloses the technique where a voltage of a main power source and a reference voltage are compared to each other, and even if the main power source is selected when the voltage of the main power source becomes lower than a voltage of a backup power source, an electric current does not flow into a load from the backup power source. Patent document 4 discloses the technique of switching power sources using relays in the constitution where the diode OR connection is adopted. Patent document 5 discloses the technique where a means for the determination of the occurrence of a failure is provided, and when a failure occurs in one system, it is possible to prevent the failure from affecting other systems.

CITATION LIST

Patent Document

Patent document 1: JP-A-9-19085
Patent document 2: JP-A-10-320081
Patent document 3: JP-A-2008-86100
Patent document 4: JP-A-2008-99404
Patent document 5: JP-A-2012-5208

SUMMARY OF INVENTION

Technical Problem

In the techniques disclosed in patent document 1 to patent document 5, by controlling turning on or off of the electronic switch or by switching the relays, the supply source of a power source is switched. Accordingly, in the techniques disclosed in the above-mentioned patent documents excluding patent document 2, when an erroneous operation or a failure occurs in a logic circuit or a microcomputer which generates a control signal for switching power sources or in relays, there arises a drawback that an operation of electric equipment is stopped due to the interruption of the supply of a power source.

To cope with such a drawback, in the technique disclosed in patent document 2, a diode is provided between a drain and a source of the switching means. Accordingly, there may be a case where even when the switching means is turned off due to an erroneous operation of the logic circuit or the like, a power source can be continuously supplied to a load through the diode. However, the mere provision of the diode brings about a situation where after the power source is switched, a voltage is supplied to the power source before switching from the power source after switching and hence, the power source after switching is consumed wastefully thus giving rise to a drawback that reliability of the power source switching circuit is lowered.

Further, the mere switching of a plurality of battery power sources by the techniques disclosed in patent document 1 to patent document 5 may bring about a situation where the power sources are frequently switched due to causes such as a contact defect or the like. In this case, a situation may be brought about where residual capacities of power source in the plurality of power sources are substantially simultaneously consumed thus giving rise to a drawback that the reliability of the power source switching circuit is lowered.

As has been described above, it is difficult for the conventional techniques to realize switching of power sources for continuously supplying a power source to electric equipment with high reliability.

The present invention has been made in view of the above-mentioned technical drawbacks. According to several aspects of the present invention, it is possible to provide a power source switching circuit, an artificial heart system and the like which can realize switching of power sources with high reliability.

Means for Solving the Problem (1) According to a first aspect of the present invention, there is provided a power source switching circuit for selectively connecting a first power source and a second power source where at least one of the first and second power sources is a battery power source to a load by switching the first power source and the second power source, the power source switching circuit including: a first power source connection part configured to enable the connection of the first power source thereto; a second power source connection part configured to enable the connection of the second power source thereto; a load connection part configured to enable the connection of the load thereto; a first switch part provided between the first power source connection part and the load connection part; a second switch part provided between the second power source connection part and the load connection part; and a switching control part configured to perform a switch control of the first switch part and the second switch part, wherein each one of the first switch part and the second switch part includes a plurality of field effect transistors which are serially connected in the same direction such that a cathode side of a body diode of each field effect transistor is arranged on a load connection part side, and are subjected to the switch control performed by the switching control part, and the number of plurality of field effect transistors is the number determined such that a sum of forward drop voltages of the plurality of serially connected body diodes exceeds the difference between a full charge voltage and a discharge voltage of the battery power source.

According to this aspect of the present invention, even when a switch control of the FET of the first switch part or the second switch part becomes inoperable due to an erroneous operation or a failure of the switching control part or the like, a power source can be continuously supplied to the load through the plurality of body diodes having a cathode side on a load connection part side. Accordingly, it is possible to avoid the occurrence of the situation where equipment is stopped due to the interruption of the supply of a power source thus enabling the power source switching having extremely high reliability. Further, the sum of forward drop voltages of the body diodes is larger than the difference between a full charge voltage and a discharge voltage of the battery power source and hence, there is no possibility that a voltage will be supplied to another battery power source from one battery power source. Accordingly, it is possible to further enhance reliability of power source switching without bringing about a possibility that the operation of equipment will be stopped due to the wasteful consumption of a power source.

(2) In the power source switching circuit according to the second aspect of the present invention, in the first aspect of the present invention, the second power source connection part is configured to enable the connection of a third power source which is an AC/DC power source thereto, and the switching control part performs the switch control of the first switch part and the second switch part such that the power source is switched to the third power source from the first power source so as to supply a power source to the load when the third power source is connected to the second power source connection part in a state where the first power source connected to the first power source connection part supplies a power source to the load.

According to this aspect of the invention, the second power source connection part enables the connection of the battery power source or the AC/DC power source thereto. Further, when the AC/DC power source is connected to the second power source connection part in a state where a power source is supplied to the load by the battery power source, the power source is switched to the AC/DC power source so that a power source is supplied to the load. According to this aspect of the present invention, in addition to the above-mentioned advantageous effect, the AC/DC power source by which it becomes unnecessary to worry about a residual capacity of power source can be used with priority over the battery power source and hence, stoppage of equipment due to the interruption of the supply of a power source can be avoided whereby the reliability of power source switching can be enhanced.

(3) The power source switching circuit according to the third aspect of the present invention includes, in the second aspect of the present invention, a second power source detection part which detects a supply voltage of the power source connected to the second power source connection part, and the switching control part performs a switch control of the first switch part and the second switch part such that the power source is switched to the third power source from the first power source so as to supply a power source to the load when the connection of the third power source to the second power source connection part is detected based on a detection result of the second power source detection part.

According to this aspect of the invention, the connection of the AC/DC power source is detected based on a supply voltage of the power source connected to the second power source connection part and hence, the power source switching circuit which acquires the above-mentioned advantageous effects can be realized with an extremely simplified constitution.

(4) In the power source switching circuit according to the fourth aspect of the present invention, in the third aspect of the present invention, the second power source detection part compares a supply voltage of the third power source and an AC/DC power source detection level with each other, and detects the connection of the third power source when the supply voltage of the third power source is higher than or equal to the AC/DC power source detection level.

According to this aspect of the present invention, the connection of the AC/DC power source is detected by comparing the supply voltage of the third power source and a predetermined AC/DC power source detection level and hence, the detection of the connection of the AC/DC power source can be performed by a comparator having an extremely simplified constitution.

(5) The power source switching circuit according to the fifth aspect of the present invention includes, in the third aspect or the fourth aspect of the present invention: a charge power source generation part which generates a charge power source based on a voltage supplied to the load connection part; and a first charge control switch part provided between the charge power source generation part and the first power source connection part, wherein the switching control part performs the switch control of the first charge control switch part so as to supply the charge power source to the first power source connection part when the switching control part detects the connection of the third power source to the second power source connection part.

According to this aspect of the invention, when the power source is switched to the AC/DC power source with priority over the battery power source, charging is performed by supplying the charge power source generated by the AC/DC power source to the batter power source through the first charge control switch part. According to this aspect, charging of the battery power source is performed by the AC/DC power source after the power source is switched to the AC/DC power source and hence, the AC/DC power source is ready for next opportunity of use of the battery power source while preventing overcharging of the AC/DC power source.

(6) The power source switching circuit according to the sixth aspect of the present invention includes, in the fifth aspect of the present invention, a first power source detection part which detects a voltage of the first power source connection part, wherein the switching control part performs a switch control of the first charge control switch part so as to stop the supply of the charge power source to the first power source connection part when a supply voltage of the power source connected to the first power source connection part is higher or equal to a charge completion voltage which is higher than the full charge voltage.

According to this aspect of the present invention, during a period where the battery power source is charged after the power source is switched to the AC/DC power source, overcharging is prevented by monitoring a supply voltage of the battery power source. Accordingly, it is possible to realize power source switching with higher reliability.

(7) The power source switching circuit according to the seventh aspect of the present invention includes, in the fifth aspect or the sixth aspect of the present invention, a second charge control switch part provided between the charge power source generation part and the second power source connection part, wherein the switching control part performs a switch control of the second charge control switch part so as to supply the charge power source to the second power source connection part when the switching control part detects the connection of the third power source to the first power source connection part.

According to this aspect of the present invention, not only when the battery power source is connected to the first power source connection part and the AC/DC power source is connected to the second power source connection part, but also when the battery power source is connected to the second power source connection part and the AC/DC power source is connected to the first power source connection part, charging of the battery power source by the AC/DC power source is performed and hence, the AC/DC power source is ready for next opportunity of use of the battery power source.

(8) In the power source switching circuit according to the eighth aspect of the present invention, in the seventh aspect of the pre sent invention, the switching control part performs a switch control of the second charge control switch part so as to stop the supply of the charge power source to the second power source connection part when a voltage of the second power source connection part is higher or equal to a charge completion voltage which is higher than the full charge voltage.

According to this aspect of the present invention, when the battery power source is connected to one of the first power source connection part and the second power source connection part and the AC/DC power source is connected to the other power source connection part, charging of the battery power source is performed by the AC/DC power source and hence, the AC/DC power source is ready for next opportunity of use of the battery power source while preventing overcharging of the AC/DC power source.

(9) In the power source switching circuit according to the ninth aspect of the present invention, in any one of the first to eighth aspects of the present invention, the switching control part is configured to continue the supply of a power source to the load by the first power source when the second power source is connected to the second power source connection part in a state where the first power source connected to the first power source connection part supplies power source to the load.

In this aspect of the present invention, when the battery power source is connected to the second power source connection part, the supply of a power source to the load by the battery power source connected to the first power source connection part is continued as it is. Accordingly, it is possible to avoid the occurrence of the situation where switching is frequently performed every time the battery power source is connected and, as a result, residual capacities of both battery power sources are consumed approximately simultaneously so that the power sources are extinguished leading to a stoppage of equipment. Accordingly, the reliability of power source switching circuit can be enhanced.

(10) According to a tenth aspect of the present invention, there is provided a power source switching circuit for selectively connecting a first power source and a second power source where the first and second power sources are battery power sources to a load by switching the first power source and the second power source, the power source switching circuit including: a first power source connection part configured to enable the connection of the first power source thereto; a second power source connection part configured to enable the connection of the second power source thereto; a load connection part configured to enable the connection of the load thereto; a first switch part provided between the first power source connection part and the load connection part; a second switch part provided between the second power source connection part and the load connection part; and a switching control part configured to perform a switch control of the first switch part and the second switch part, wherein the switching control part is configured to continue the supply of a power source to the load by the first power source when the second power source is connected to the second power source connection part in a state where the first power source connected to the first power source connection part supplies power source to the load.

According to this aspect of the present invention, even when a switch control of the FET of the first switch part or the second switch part becomes inoperable due to an erroneous operation or a failure of the switching control part or the like, power source can be continuously supplied to the load through the plurality of body diodes having a cathode side on a load connection part side. Accordingly, it is possible to avoid the occurrence of the situation where equipment is stopped due to the interruption of the supply of a power source thus enabling switching of power sources having extremely high reliability. Further, according to this aspect, when the batter power source is connected to the second power source connection part, the supply of a power source to the load by the battery power source connected to the first power source connection part is continued as it is. Accordingly, it is possible to avoid the occurrence of the situation where switching is frequently performed every time the battery power source is connected and, as a result, residual capacities of both battery power sources are consumed approximately simultaneously so that the power sources are extinguished leading to a stoppage of equipment. Accordingly, the reliability of switching of power sources can be enhanced.

(11) In the power source switching circuit according to the eleventh aspect of the present invention, in the ninth or tenth aspect of the present invention, the switching control part is configured to perform a switch control of the first switch part and the second switch part so as to supply a power source to the load by switching the power source to the second power source from the first power source when a supply voltage from the first power source becomes less than the discharge voltage.

In this aspect of the present invention, the supply of a power source to the load by the battery power source connected to the first power source connection part is continued when the battery power source is connected to the second power source connection part. On the other hand, when a residual capacity of the battery power source connected to the first power source connection part becomes small due to the supply of a power source from the battery power source so that the battery power source connected to the first power source connection part is brought into a charge required state, the power source is switched to the battery power source connected to the second power source connection part. Accordingly, in addition to the above-mentioned advantageous effects, it is possible to continue the supply of a power source by switching the supply source to the new battery power source before a residual capacity of power source in the battery power source is consumed so that the supply of a power source is stopped.

(12) According to a twelfth aspect of the present invention, an artificial heart system includes: a blood pump which assists the flow of blood in a heart; a blood pump control part which controls the blood pump; and the power source switching circuit described in any one of the first to eleventh aspects of the present invention which supplies power source to the blood pump and the blood pump control part.

According to this aspect of the present invention, it is possible to provide the artificial heart system where even when a switch control of the FET of the first switch part or the second switch part becomes inoperable due to an erroneous operation or a failure of the switching control part or the like, a power source is switched with high reliability so as to continuously supply a power source.

(13) The artificial heart system according to a thirteenth aspect of the present invention includes, in the twelfth aspect of the present invention, a display part which displays a connection state of the power source in the first power source connection part, a connection state of the power source in the second power source connection part, a power source supply state from the power source connected to the first power source connection part to the load, and a power source supply state from the power source connected to the second power source connection part to the load.

According to this aspect of the present invention, a connection state and a power source supply state of the power source connected to the above-mentioned power source switching circuit are displayed and hence, a patient does not feel anxiety about the sudden interruption of the supply of a power source thus enhancing reliability of the artificial heart system.

BRIEF DESCRIPTIONS OF THE DRAWINGS

FIG. 6 is a view for explaining an operation of a first comparator.

FIG. 10 is a view schematically showing a second display example of the display part according to the embodiment of the present invention.

BEST MODE FOR CARRYING OUT THE INVENTION

Hereinafter, an embodiment of the present invention is explained in detail in conjunction with drawings. The embodiment explained hereinafter does not unduly limit contents of the present invention described in Claims. Further, it is not intended to limit the scope of the present invention to the case where all constitutions explained hereinafter are indispensable constitutional elements for overcoming drawbacks of the present invention.

[Artificial Heart System]

Figure 1:
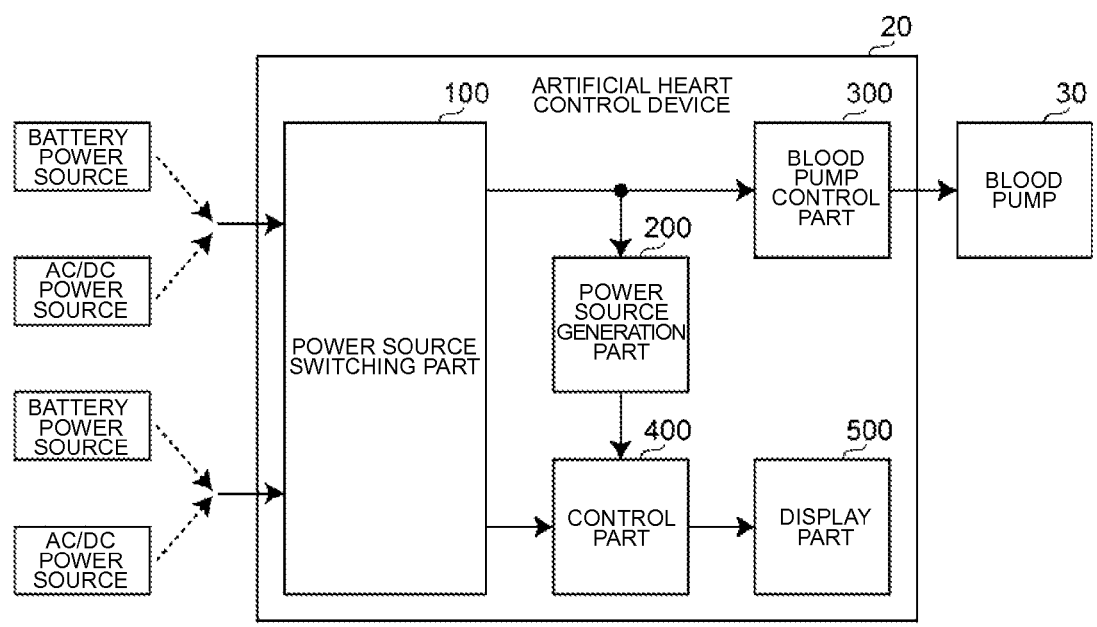
FIG. 1 is a block diagram of a constitutional example of an artificial heart system according to one embodiment of the present invention.

FIG. 1 is a block diagram of a constitutional example of an artificial heart system according to one embodiment of the present invention. The artificial heart system shown in FIG. 1 is, aiming at BTT (Bridge To Transplant), mounted on a patient waiting for a heart transplant, and the circulation of blood of the patient is assisted by a blood pump. With the use of such an artificial heart system, the patient waiting for a heart transplant is able to wait for a long period for a donor who is compatible with the patient.

An artificial heart system 10 includes: an artificial heart control device (artificial heart controller) 20; and a blood pump (a pump, a motor, an artificial heart pump) 30 which assists the flow of blood in a heart of the patient. The blood pump 30 and the artificial heart control device 20 are connected with each other by way of a cable not shown in the drawing.

The blood pump 30 functions as a left ventricular assist device (LVAD) which assists a function of a left ventricle of the heart of a patient. The blood pump 30 is a continuous-flow-type blood pump where the flow of blood to be circulated is a continuous flow.

Figure 2:
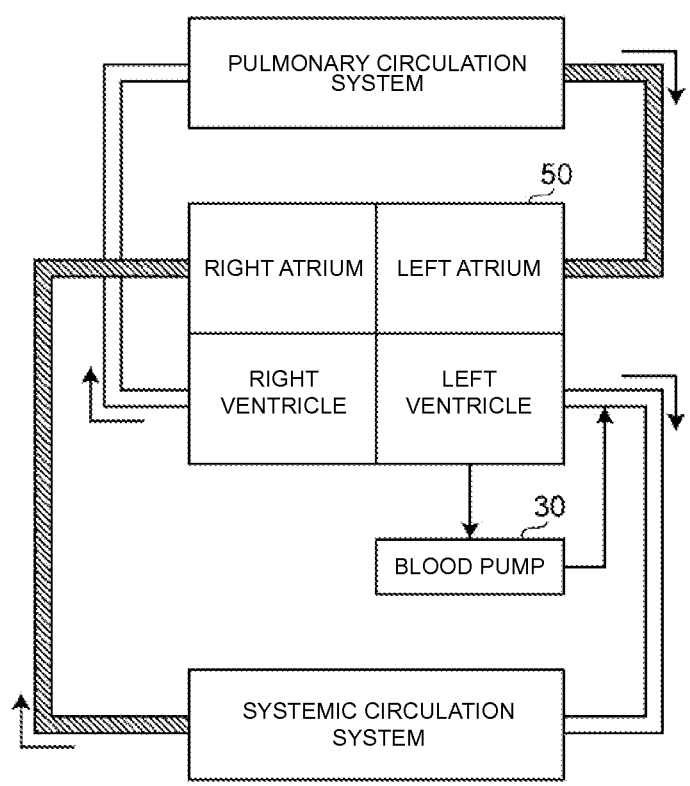
FIG. 2 is an explanatory view of a blood pump according to the embodiment of the present invention.

FIG. 2 is an explanatory view of the blood pump 30 according to this embodiment. FIG. 2 schematically shows the heart of a patient and a circulation system in his body.

The heart 50 of a patient is partitioned into a left atrium, a left ventricle, a right atrium and a right ventricle. The right atrium and the right ventricle have a function of circulating blood through a pulmonary circulation system, and the left atrium and the left ventricle have a function of circulating blood through a systemic circulation system. That is, the blood which is returned to the heart from the systemic circulation system through a superior vena cava and an inferior vena cava is stored in the right atrium and, thereafter, is sent to the right ventricle. The blood which is sent to the right ventricle circulates through the pulmonary circulation system through a pulmonary trunk by the pumping action of the right ventricle, and is brought into a state where the blood contains oxygen. The blood which is returned to the heart from the pulmonary circulation system through pulmonary veins is stored in the left atrium and, thereafter, is sent to the left ventricle. The blood which is sent to the left ventricle circulates through the systemic circulation system through a main artery by the pumping action of the left ventricle. The blood pump 30 according to this embodiment, to assist the function of the left ventricle, sucks in the blood which is fed to the left ventricle, and feeds the blood to the main artery.

In this embodiment, the blood pump 30 is embedded in a patient's body, and the artificial heart control device 20 is arranged outside the patient's body. However, some of or all functional parts of the artificial heart control device 20 may be mounted in the patient's body. As a cable for connecting the artificial heart control device 20 and the blood pump 30 to each other, a lubrication-fluid feed-side pipe and a lubrication-fluid return-side pipe are provided to the blood pump 30 thus forming a circulation passage for the lubrication fluid. Further, the cable includes a signal line as a communication cable. A drive current to be supplied to the blood pump 30 from the artificial heart control device 20 is transmitted through the signal line.

The blood pump 30 is controlled by the artificial heart control device 20. The artificial heart control device 20 includes: a power source switching part (power source switching circuit) 100; a power source generation part 200; a blood pump control part 300; a control part 400; and a display part 500.

The power source switching part 100 selects either one of power sources of two systems to be connected to the power source switching part 100, and connects the power source of the selected system to a load which is constituted of the blood pump control part 300, the power source generation part 200, and the blood pump 30. Due to such a constitution, the power source is continuously supplied to the load. Such a power source switching part 100 has two power source connectors, and respective power source connectors are configured to enable the connection of a battery power source or an AC/DC power source thereto. Here, the AC/DC power source means a power source which is obtained by converting a commercial power source which is an AC power source into a DC voltage (for example, 18V) using an AC/DC adaptor.

The power source generation part 200 generates a voltage of a predetermined level (for example, 3V or 5V) which is supplied to the control part 400 and the display part 500 from the power source which is selected by switching by the power source switching part 100.

The blood pump control part 300, in a state where a power source selected by switching by the power source switching part 100 is supplied to the blood pump control part 300, generates a drive current (a drive signal in broad meaning of the term) which drives the blood pump 30, and controls a rotational speed of the blood pump 30.

A voltage generated by the power source generation part 200 is supplied to the control part 400, and the control part 400 controls the whole artificial heart control device 20 including a display control of the display part 500 based on an internal signal of the power source switching part 100.

The display part 500 displays various operation states (for example, a connection state and a power source supply state of the power source) of the artificial heart system 10 by a display control performed by the control part 400.

[Power Source Switching Circuit]

Figure 3:
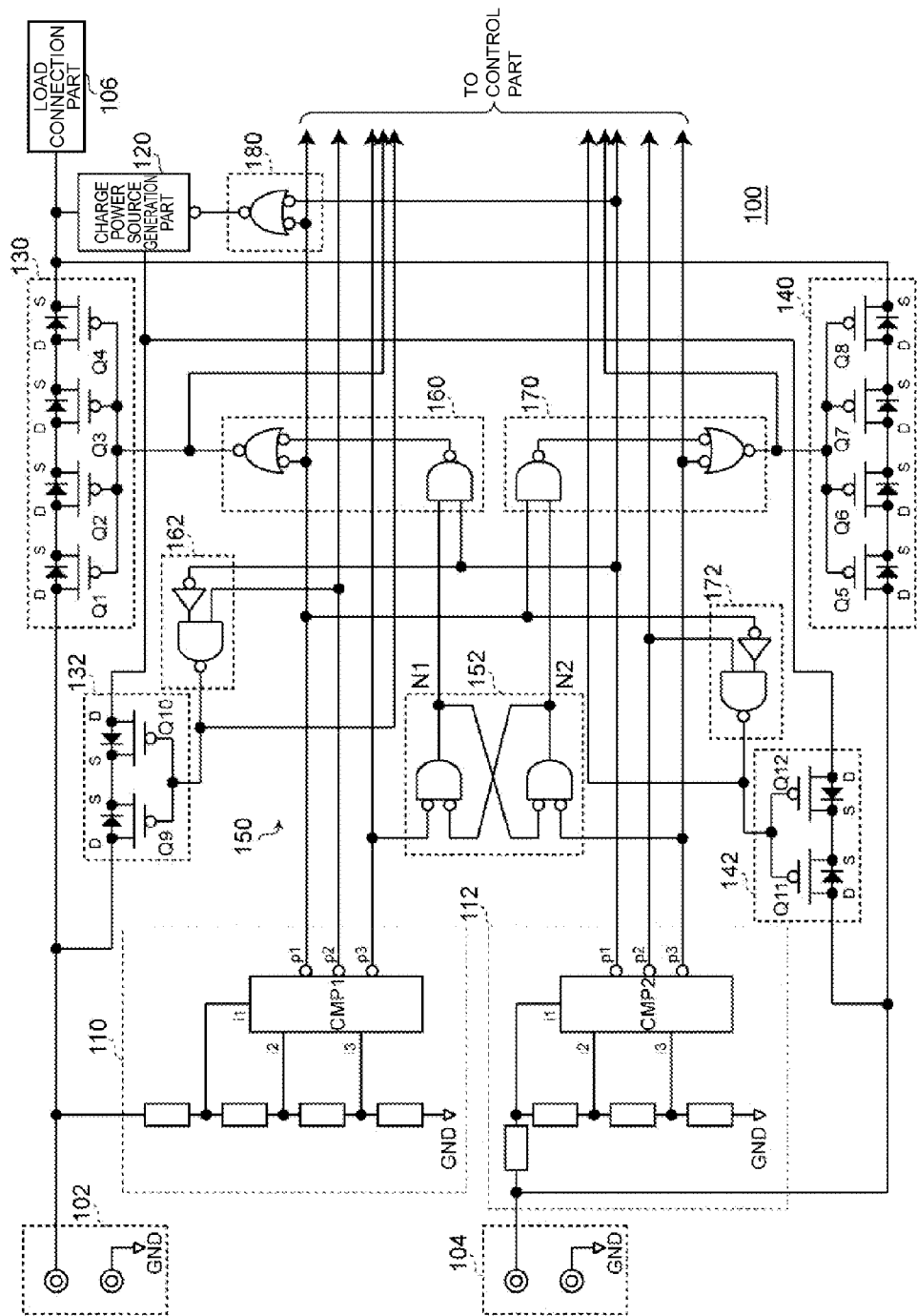
FIG. 3 is a circuit diagram of a constitutional example of a power source switching part according to the embodiment of the present invention.

FIG. 3 is a circuit diagram of a constitutional example of the power source switching part 100 shown in FIG. 1 which constitutes a power source switching circuit of this embodiment. In this embodiment, the explanation is made hereinafter with respect to the case where the power source switching part 100 is a switching part which switches power sources of two systems. However, the power source switching part 100 may be configured to switch power sources of three or more systems.

The power source switching part 100 includes: a first power source connector (first power source connection part) 102; a second power source connector (second power source connection part) 104; a load connection part 106; a first power source detection part 110; a second power source detection part 112; and a charge power source generation part 120. Further, the power source switching part 100 includes: a first switch part 130; a first charge control switch part 132; a second switch part 140; a second charge control switch part 142; and a switching control part 150.

The first power source connector 102 is configured to enable the connection of a battery power source (first power source) or an AC/DC power source thereto.

The second power source connector 104 is also configured to enable the connection of a battery power source (second power source) or an AC/DC power source (third power source) thereto.

The load connection part 106 is configured to enable the connection of a load which is constituted of the blood pump control part 300, the power source generation part 200, and the blood pump 30 thereto.

The first power source detection part 110 detects a type and a state of a power source connected to the first power source connector 102 based on a supply voltage of a power source connected to the first power source connector 102. To be more specific, the first power source detection part 110 detects whether a power source connected to the first power source connector 102 is an AC/DC power source or a battery power source. The first power source detection part 110 also detects whether the battery power source is in a full charge state or in a charge required state when it is detected that the power source is a battery power source.

The second power source detection part 112 detects a type and a state of a power source connected to the second power source connector 104 based on a supply voltage of a power source connected to the second power source connector 104. To be more specific, the second power source detection part 112 detects whether a power source connected to the second power source connector 104 is an AC/DC power source or a battery power source. The second power source detection part 112 also detects whether the battery power source is in a full charge state or in a charge required state when it is detected that the power source is a battery power source. The first power source detection part 110 and the second power source detection part 112 have the substantially same constitution.

The first switch part 130 is provided between the first power source connector 102 and the load connection part 106. The first switch part 130 includes a plurality of p-type FETs which are switch-controlled by the switching control part 150, and the plurality of FETs are serially connected in the same direction such that a cathode side of a body diode (parasitic diode) of each FET is arranged on a load connection part 106 side. Here, the number of plurality of FETs which are serially connected to each other is the number determined such that a sum of forward drop voltages of the body diodes of the respective FETs exceeds the difference between a full charge voltage and a discharge voltage of the battery power source connected to the first power source connector 102.

The second switch part 140 is provided between the second power source connector 104 and the load connection part 106. The second switch part 140 includes a plurality of p-type FETs which are switch-controlled by the switching control part 150, and the plurality of FETs are serially connected to each other in the same direction such that a cathode side of a body diode of each FET is arranged on a load connection part 106 side. Here, the number of plurality of FETs which are serially connected to each other is set such that a sum of forward drop voltages of the body diodes of the respective FETs exceeds the difference between a full charge voltage and a discharge voltage of the battery power source connected to the second power source connector 104.

The charge power source generation part 120 is connected to a connection node between a connection node between the first switch part 130 and the second switch part 140 and the load connection part 106, and generates a charge power source based on a voltage supplied to the load connection part 106 when the power source switching part 100 is operated.

The first charge control switch part 132 is provided between the first power source connector 102 and the charge power source generation part 120. The first charge control switch part 132 includes FETs Q9, Q10 which are connected to each other such that body diodes of the FETs Q9, Q10 are arranged in opposite directions from each other.

The second charge control switch part 142 is provided between the second power source connector 104 and the charge power source generation part 120. The second charge control switch part 142 includes FETs Q11, Q12 which are connected to each other such that body diodes of the FETs Q11, Q12 are arranged in opposite directions from each other.

The switching control part 150 controls the first switch part 130, the first charge control switch part 132, the second switch part 140, the second charge control switch part 142, and the charge power source generation part 120 based on detection results of the first power source detection part 110 and the second power source detection part 112. To be more specific, the switching control part 150 performs a switch control of the first switch part 130 and the second switch part 140 such that either one of the first power source connector 102 and the second power source connector 104 which is connected to the power source switching part 100 ahead is connected to the load connection part 106.

Such a switching control part 150 includes: an arrival order holding part 152; a first priority connection control part 160; a first charge control part 162; a second priority connection control part 170; a second charge control part 172; and a charge power source control part 180.

The arrival order holding part 152 holds a state corresponding to the power source connector to which a battery power source or an AC/DC power source is connected ahead out of the first power source connector 102 and the second power source connector 104. Such an arrival order holding part 152 may be constituted of an RS-type flip flop as shown in FIG. 3, for example.

The first priority connection control part 160, when the first power source detection part 110 or the second power source detection part 112 detects the connection of an AC/DC power source, performs a switch control of the first switch part 130 while masking the above-mentioned state held by the arrival order holding part 152. To be more specific, when the AC/DC power source is connected to the first power source connector 102, the first priority connection control part 160 can perform a control of turning on the first switch part 130 regardless of a state held by the arrival order holding part 152.

The first charge control part 162, when an AC/DC power source is connected to the second power source connector 104, performs a charge control of a battery power source connected to the first power source connector 102. To be more specific, the first charge control part 162 controls the first charge control switch part 132 such that the charging of a battery power source connected to the first power source connector 102 is performed by the AC/DC power source connected to the second power source connector 104. In this operation, the first charge control part 162 controls the first charge control switch part 132 such that the first charge control switch part 132 is turned on when a supply voltage of the battery power source connected to the first power source connector 102 is less than a charge completion voltage.

The second priority connection control part 170, when the first power source detection part 110 or the second power source detection part 112 detects the connection of an AC/DC power source, performs a switch control of the second switch part 140 while masking the above-mentioned state held by the arrival order holding part 152. To be more specific, when the AC/DC power source is connected to the second power source connector 104, the second priority connection control part 170 can perform a control of turning on the second switch part 140 regardless of a state held by the arrival order holding part 152.

The second charge control part 172, when an AC/DC power source is connected to the first power source connector 102, performs a charge control of a battery power source connected to the second power source connector 104. To be more specific, the second charge control part 172 controls the second charge control switch part 142 such that the charging of the battery power source connected to the second power source connector 104 is performed by the AC/DC power source connected to the first power source connector 102. In this operation, the second charge control part 172 controls the second charge control switch part 142 such that the second charge control switch part 142 is turned on when a supply voltage of the battery power source connected to the second power source connector 104 is less than a charge completion voltage.

The charge power source control part 180 controls the charge power source generation part 120 such that an operation of the charge power source generation part 120 is turned on when the AC/DC power source is connected to the first power source connector 102 or the second power source connector 104.

In the power source switching part 100 having such a constitution, there may be a case where an erroneous operation or a failure occurs in any one of the first power source detection part 110, the second power source detection part 112, and the switching control part 150 so that the first switch part 130 and the second switch part 140 cannot be turned on. In this respect, according to this embodiment, the body diodes are serially connected to each other in the same direction such that the cathode side of each body diode is arranged on a load connection part 106 side and hence, it is possible to continuously supply a power source to a load from a power source which is connected to either one of the power source connectors. Accordingly, it is possible to avoid the occurrence of the situation where equipment is stopped due to the interruption of the supply of a power source thus enabling the switching of power sources having extremely high reliability. Further, the sum of forward drop voltages of the body diodes is larger than the difference between a full charge voltage and a discharge voltage of the battery power source and hence, there is no possibility that a voltage is supplied to another battery power source from one battery power source. Accordingly, it is possible to further enhance reliability of switching of power sources without bringing about a possibility that the operation of equipment is stopped due to the wasteful consumption of a power source.

Further, when the battery power source is connected to the second power source connector 104 in a state where the battery power source is connected to the first power source connector 102 ahead so that a power source is supplied to the load, the switching control part 150 does not perform the switching of the power source. That is, the switching control part 150 continues the supply of the power source to the load by the battery power source connected to the first power source connector 102 as it is. Accordingly, it is possible to avoid the occurrence of the situation where switching is frequently performed every time the battery power source is connected and, as a result, residual capacities of both battery power sources are consumed approximately simultaneously. Accordingly, the reliability of switching of power sources can be enhanced.

Thereafter, the supply voltage of the battery power source connected to the first power source connector 102 is lowered. When the supply voltage becomes less than a discharge voltage, the switching control part 150 performs a switch control of the first switch part 130 and the second switch part 140 so as to supply a power source to the load by switching the power source from the battery power source connected to the first power source connector 102 to the battery power source connected to the second power source connector 104. Accordingly, it is possible to continue the supply of a power source by switching the supply source to the new battery power source before a residual capacity in the battery power source is consumed so that the supply of a power source is stopped.

Further, when the AC/DC power source is connected to the second power source connector 104 in a state where the battery power source is connected to the first power source connector 102 ahead so that a power source is supplied to the load, the switching control part 150 performs a switch control of the first switch part 130 and the second switch part 140 so as to supply a power source to the load by switching the power source from the battery power source to the AC/DC power source. Accordingly, the AC/DC power source with which it is unnecessary to worry about a residual capacity of power source can be used with priority over the battery power source and hence, stoppage of equipment due to the interruption of the supply of a power source can be avoided whereby the reliability of switching of power sources can be enhanced.

At this stage of operation, the switching control part 150 performs a switch control of the first charge control switch part 132 so as to supply a charge power source generated by the charge power source generation part 120 to the battery power source connected to the first power source connector 102. When a supply voltage of the battery power source connected to the first power source connector 102 becomes more than or equal to or a charge completion voltage, the switching control part 150 performs a switch control of the first charge control switch part 132 so as to stop the supply of the charge power source to the battery power source based on a detection result of the first power source detection part 110. Accordingly, charging of the battery power source is performed by the AC/DC power source after the power source is switched to the AC/DC power source and hence, the AC/DC power source is ready for next opportunity of use of the battery power source while preventing overcharging of the AC/DC power source.

Hereinafter, the manner of operation of the power source switching part 100 shown in FIG. 3 is explained specifically. In this embodiment, assume that a supply voltage of the AC/DC power source is 18.0V, a charge completion voltage (use start voltage) of the battery power source is 16.8V, a full charge voltage is 16.0V which is lower than the charge completion voltage, and a discharge voltage (use stop determination voltage) is 13.8V.

In FIG. 3, the first power source detection part 110 compares a supply voltage of a power source connected to the first power source connector 102 and an AC/DC power source detection voltage V1 (17.5V) which is lower than a supply voltage of the AC/DC power source, and detects whether or not the connected power source is the AC/DC power source.

The first power source detection part 110 detects whether or not the battery power source is in a full charge state by comparing the supply voltage of the power source connected to the first power source connector 102 and a charge completion voltage V2.

Further, the first power source detection part 110 detects whether or not the battery power source is in a charge required state by comparing the supply voltage of the power source connected to the first power source connector 102 and a discharge voltage V3.

Figure 4:
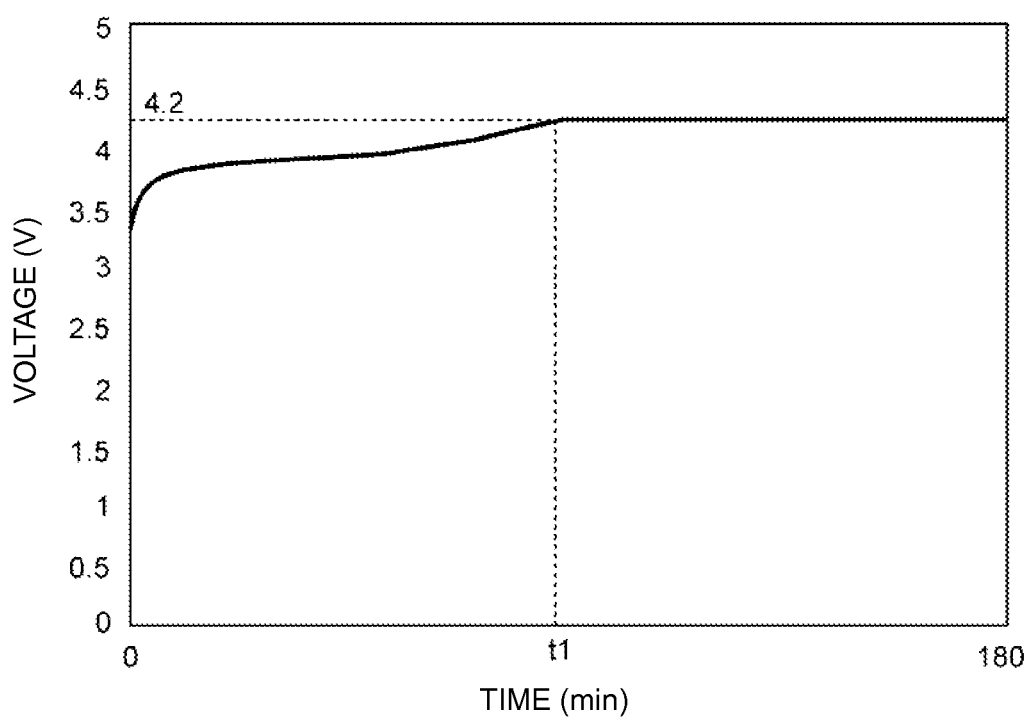
FIG. 4 is an explanatory view of a charge completion voltage of a battery power source according to the embodiment of the present invention.

FIG. 4 is a graph for explaining a charge completion voltage of the battery power source connected to the first power source connector 102 or the second power source connector 104. In FIG. 4, a voltage is taken on an axis of ordinates and a time is taken on an axis of abscissas. FIG. 4 shows one example of a charging characteristic per one cell when the battery power source is charged with an electric current which is 0.5 times as large as a rated current of the battery power source.

When the charging of the battery power source in a discharge state is started with a predetermined electric current, an output voltage (cell voltage) of the battery power source is increased. When a time t1 elapses and an output voltage reaches a preset voltage (4.2V, for example) with respect to the battery power source, a succeeding output voltage becomes a constant voltage, and the constant voltage is assumed as a charge completion voltage. In this embodiment, for example, assume that four cells each having the charging characteristic shown in FIG. 4 are serially connected to each other and hence, the charge completion voltage V2 becomes 16.8V (=4.2V×4). Accordingly, by detecting whether or not an output voltage of the battery power source is a charge completion voltage which is a use start voltage at which the use of the battery power source is started, it is possible to determine whether or not the battery power source can be used as the battery power source in a full charge state. An output voltage of such a battery power source in a full charge state is generally lower than the charge completion voltage V2 and hence, in this embodiment, the output voltage is set to 16.0V as a full charge voltage.

Figure 5:
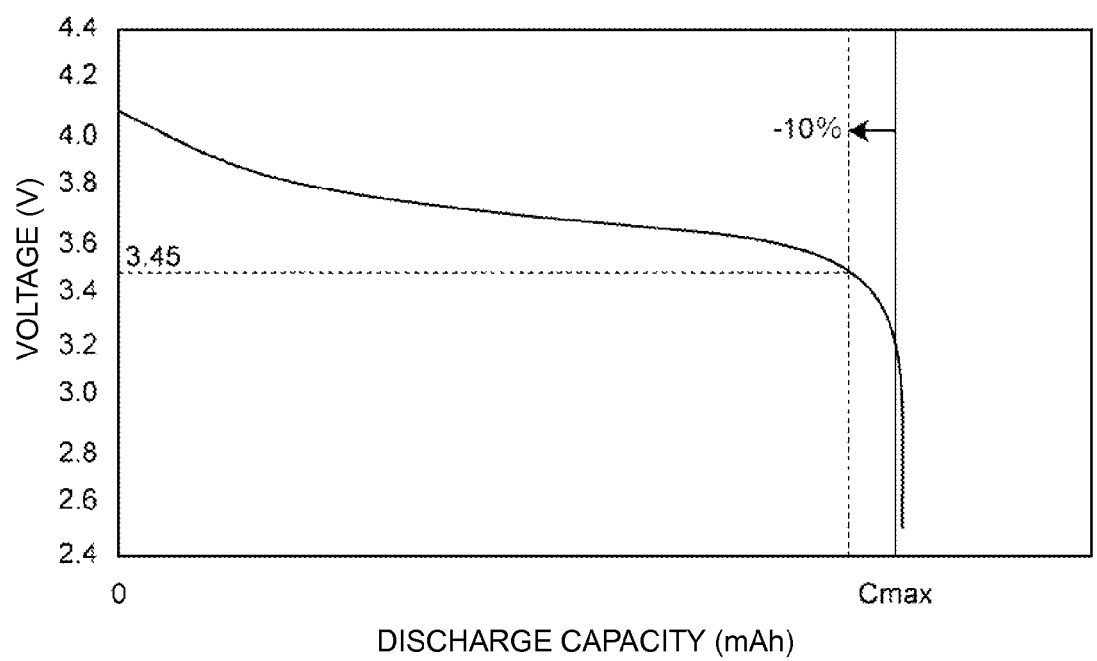
FIG. 5 is an explanatory view of a discharge voltage of the battery power source according to the embodiment of the present invention.

FIG. 5 is a graph for explaining a discharge voltage of the battery power source connected to the first power source connector 102 or the second power source connector 104. In FIG. 5, a voltage is taken on an axis of ordinates and a discharge capacity of the battery power source is taken on an axis of abscissas. FIG. 5 shows one example of a discharge characteristic per one cell when the battery power source is discharged with an electric current which is 0.5 times as large as a rated current of the battery power source.

When the battery power source in a charge completion state is discharged with a predetermined electric current, an output voltage (a cell voltage) of the battery power source is lowered. When a discharge capacity reaches Cmax, the output voltage is rapidly lowered. Accordingly, an output voltage (3.45V, for example) at a point of time that a residual capacity of the battery power source is 90% of the discharge capacity Cmax is set as a discharge voltage, for example. In this embodiment, for example, assume that four cells each having the discharge characteristic shown in FIG. 5 are serially connected to each other, and a voltage of 13.8V (=3.45V×4) is adopted as the discharge voltage V3.

To detect the above-mentioned various kinds of voltages, the first power source detection part 110 shown in FIG. 3 includes a first comparator CMP1 having monitor input terminals i1 to i3 and output terminals p1 to p3. Detection-use voltages which are generated based on a supply voltage of a power source connected to the first power source connector 102 are inputted to the respective monitor input terminals i1 to i3, and output signals corresponding to the supply voltage of the power source are outputted from the output terminals p1 to p3 respectively.

FIG. 6 is a table for explaining the manner of operation of the first comparator CMP1. In FIG. 6, a supply voltage of a power source connected to the first power source connector 102 is expressed as Vin.

As shown in FIG. 6, an output signal of the output terminal p1 becomes an L level when the supply voltage Vin of the power source is more than or equal to the AC/DC power source detection voltage V1, and becomes an H level when the supply voltage Vin of the power source is less than the AC/DC power source detection voltage V1. An output signal of the output terminal p2 becomes an L level when the supply voltage Vin of the power source is more than or equal to the charge completion voltage V2, and becomes an H level when the supply voltage Vin of the power source is less than the charge completion voltage V2. An output signal of the output terminal p3 becomes an L level when the supply voltage Vin of the power source is more than or equal to the discharge voltage V3, and becomes an H level when the supply voltage Vin of the power source is less than the discharge voltage V3.

Accordingly, when an output signal of the output terminal p1 becomes an L level, it is detected that the power source connected to the first power source connector 102 is an AC/DC power source. On the other hand, when an output signal of the output terminal p1 becomes an H level, and an output signal of the output terminal p3 becomes an L level, it is detected that the power source connected to the first power source connector 102 is a battery power source.

Such a function of the first comparator CMP1 can be realized by a battery monitor circuit (MAX6782) manufactured by MAXIM Integrated, for example. The constitution and the manner of operation of the second power source detection part 112 is substantially equal to the constitution and the manner of operation of the first power source detection part 110.

As shown in FIG. 3, the first switch part 130 includes four FETs Q1 to Q4. Here, a drain of the FET Q2 is connected to a source of the FET Q1 which has a drain thereof arranged on a first power source connector 102 side, a drain of the FET Q3 is connected to a source of the FET Q2, and a drain of the FET Q4 is connected to a source of the FET Q3. A source of the FET Q4 is arranged on a load connection part 106 side. Gates of the FETs Q1 to Q4 are controlled by the switching control part 150. Assuming that a full charge voltage of the battery power source is 16.0V, a discharge voltage V3 of the battery power source is 13.8V, and forward drop voltages of the respective body diodes are 0.6V, the relationship of (16.0V−13.8V)<0.6V×4 is established.

The second switch part 140 includes, in the same manner as the first switch part 130, four TEFs Q5 to Q8. Here, a drain of the FET Q6 is connected to a source of the FET Q5 which has a drain thereof arranged on a second power source connector 104 side, a drain of the FET Q7 is connected to a source of the FET Q6, and a drain of the FET Q8 is connected to a source of the FET Q7. A source of the FET Q8 is arranged on a load connection part 106 side. Gates of the FETs Q5 to Q8 are controlled by the switching control part 150. Also with respect to the second switch part 140, in the same manner as the first switch part 130, assuming that a full charge voltage of the battery power source is 16.0V, the discharge voltage V3 of the battery power source is 13.8V, and forward drop voltages of the respective body diodes are 0.6V, the relationship of (16.0V−13.8V)<0.6V×4 is established.

Accordingly, in a state where the battery power source is connected to the first power source connector 102 and the second power source connector 104 respectively, a potential of the body diode on a cathode side becomes lower than a potential of the body diode on an anode side and hence, there is no possibility that a voltage is supplied to other battery power source from one battery power source.

Next, an example of the manner of operation of the above-mentioned power source switching part 100 is explained by reference to a timing chart. As shown in FIG. 3, in the power source switching part 100, paths from both power source connectors to the load connection part 106 are substantially equal and controls applied to the respective paths are also substantially equal. Accordingly, even when the first power source connector 102 and the second power source connector 104 are exchanged with each other, the power source switching part 100 is operated in the same manner.

Figure 7:
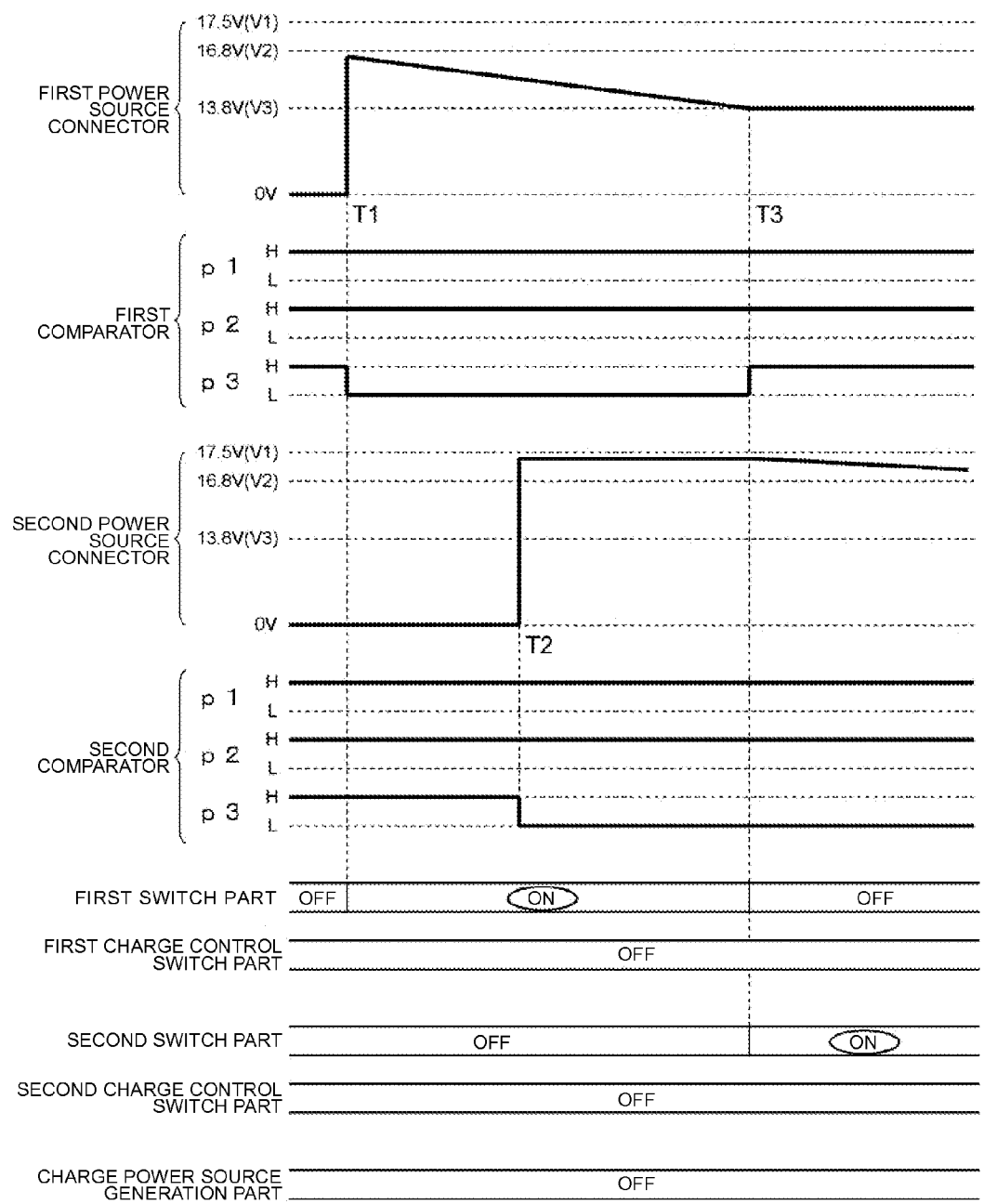
FIG. 7 is a timing chart of a first operation example of the power source switching part shown in FIG. 3.

FIG. 7 is a timing chart showing a first example of the manner of operation of the power source switching part 100 shown in FIG. 3. FIG. 7 shows one example of an operation timing of the power source switching part 100 when a battery power source is connected to the first power source connector 102 in a state where power sources are not connected to both power source connectors and, thereafter, the battery power source is connected to the second power source connector 104.

When the power source is connected to neither the first power source connector 102 nor the second power source connector 104, output signals of the output terminals p1 to p3 of the first comparator CMP1 of the first power source detection part 110 become an H level. In the same manner, output signals of the output terminals p1 to p3 of the second comparator CMP2 of the second power source detection part 112 also become an H level. At this stage of operation, a connection node N1 between the arrival order holding part 152 and the first priority connection control part 160 becomes an L level, and a connection node N2 between the arrival order holding part 152 and the second priority connection control part 170 becomes an L level. As a result, an output signal of the first priority connection control part 160 becomes an H level so that the first switch part 130 is turned off, and an output signal of the second priority connection control part 170 becomes an H level so that the second switch part 140 is turned off. An output signal of the first charge control part 162 becomes an H level so that the first charge control switch part 132 is turned off, and an output signal of the second charge control part 172 becomes an H level so that the second charge control switch part 142 is turned off. Further, an output signal of the charge power source control part 180 becomes an H level, and an operation of the charge power source generation part 120 is turned off so that a GND-level voltage is outputted.

Assume that, succeeding to the above-mentioned operation, the battery power source in a full charge state is connected only to the first power source connector 102 at a point of time T1. At this point of time T1, a full charge voltage is 16.0V and hence, output signals of the output terminals p1, p2 of the first comparator CMP1 become an H level, and an output signal of the output terminal p3 becomes an L level. Accordingly, the connection node N1 becomes an H level and hence, an output signal of the first priority connection control part 160 is changed to an L level whereby the first switch part 130 is turned on. As a result, the battery power source connected to the first power source connector 102 starts to supply a power source to the load connected to the load connection part 106.

Assume that the battery power source in a full charge state is also connected to the second power source connector 104 at a point of time T2 which comes after the point of time T1. At this the point of time T2, output signals of the output terminals p1, p2 of the second comparator CMP2 become an H level, and an output signal of the output terminal p3 of the second comparator CMP2 becomes an L level. In this case, however, the connection node N1 is held at an H level and the connection node N2 is held at an L level and hence, an output signal of the first priority connection control part 160 and an output signal of the second priority connection control part 170 are not changed. Accordingly, the switching control part 150 can continue the supply of a power source to the load by the battery power source connected to the first power source connector 102.

When the supply of a power source by the battery power source connected to the first power source connector 102 is continued, a residual capacity of the battery power source becomes small and hence, the supply voltage is gradually lowered. Then, when a supply voltage of the battery power source which has been supplying a power source to a load becomes less than the discharge voltage at a point of time T3 which comes after the point of time T2, an output signal of the output terminal p3 of the first comparator CMP1 is changed to an H level. As a result, a voltage at the connection node N1 becomes an L level and a voltage at the connection node N2 becomes an H level and hence, an output signal of the first priority connection control part 160 is changed to an H level so that the first switch part 130 is turned off and, at the same time, an output signal of the second priority connection control part 170 is changed to an L level so that the second switch part 140 is turned on. As a result, the power source is switched from the battery power source connected to the first power source connector 102 to the battery power source connected to the second power source connector 104, and the battery power source connected to the second power source connector 104 starts to supply a power source to the load connected to the load connection part 106.

Figure 8:
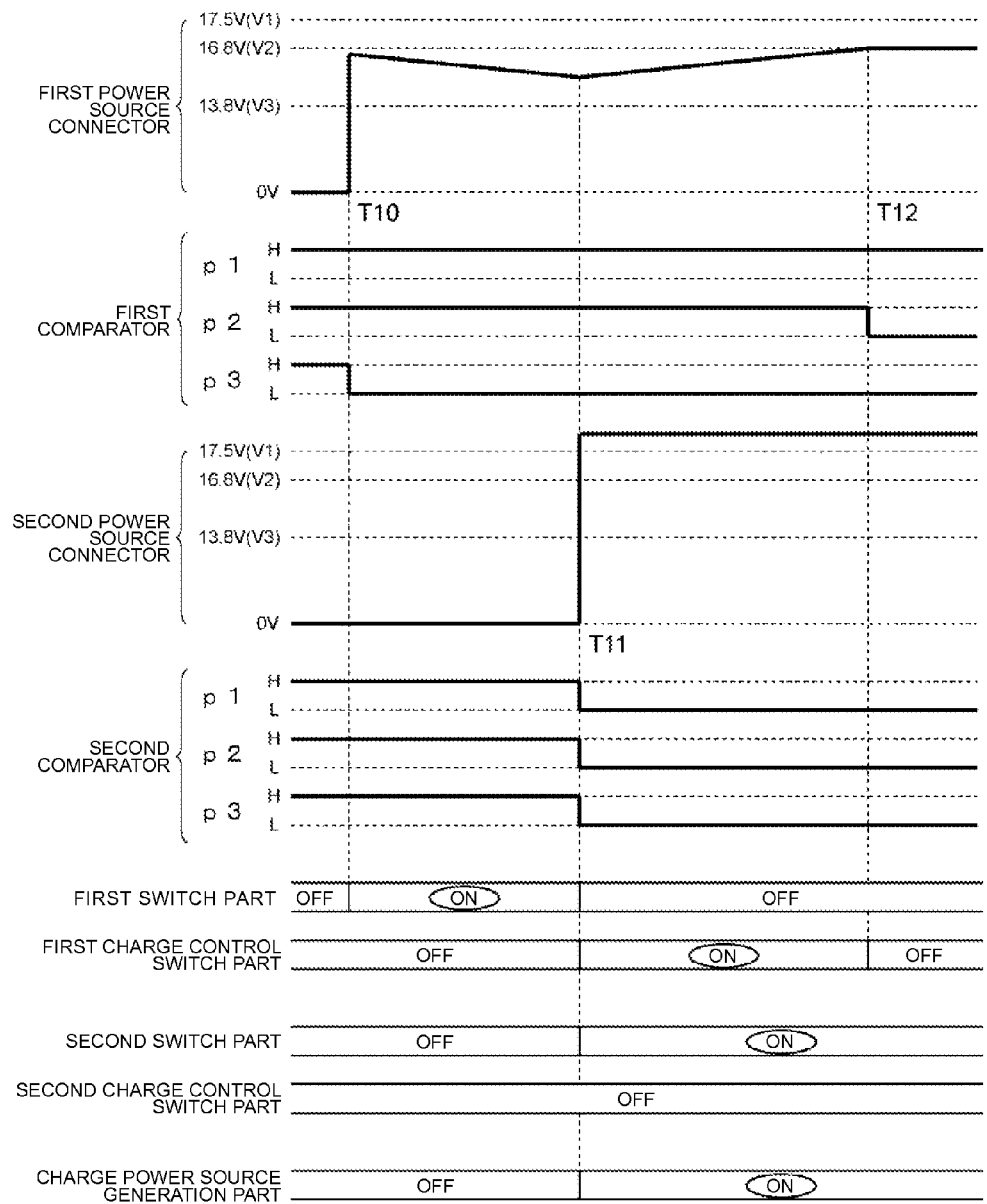
FIG. 8 is a timing chart of a second operation example of the power source switching part shown in FIG. 3.

FIG. 8 is a timing chart showing a second example of the manner of operation of the power source switching part 100 shown in FIG. 3. FIG. 8 shows one example of an operation timing of the power source switching part 100 when a battery power source is connected to the first power source connector 102 in a state where power sources are connected to neither one of the power source connectors and, thereafter, the AC/DC power source is connected to the second power source connector 104.

When the power source is connected to neither the first power source connector 102 nor the second power source connector 104, output signals of the output terminals p1 to p3 of the first comparator CMP1 of the first power source detection part 110 become an H level. In the same manner, output signals of the output terminals p1 to p3 of the second comparator CMP2 of the second power source detection part 112 also become an H level. At this stage of operation, a connection node N1 becomes an L level, and a connection node N2 becomes an L level. As a result, an output signal of the first priority connection control part 160 becomes an H level so that the first switch part 130 is turned off, and an output signal of the second priority connection control part 170 becomes an H level so that the second switch part 140 is turned off. An output signal of the first charge control part 162 becomes an H level so that the first charge control switch part 132 is turned off, and an output signal of the second charge control part 172 becomes an H level so that the second charge control switch part 142 is turned off. Further, an output signal of the charge power source control part 180 becomes an H level, and an operation of the charge power source generation part 120 is turned off so that a GND-level voltage is outputted.

Assume that, succeeding to the above-mentioned operation, the battery power source in a full charge state is connected only to the first power source connector 102 at a point of time T10. At this point of time T10, output signals of the output terminals p1, p2 of the first comparator CMP1 become an H level, and an output signal of the output terminal p3 becomes an L level. Accordingly, the connection node N1 becomes an H level and hence, an output signal of the first priority connection control part 160 is changed to an L level whereby the first switch part 130 is turned on. As a result, the battery power source connected to the first power source connector 102 starts to supply a power source to the load connected to the load connection part 106.

Assume that the AC/DC power source is also connected to the second power source connector 104 at a point of time T11 which comes after the point of time T10. At this point of time T11, output signals of the output terminals p1 to p3 of the second comparator CMP2 become an L level. Accordingly, an output signal of the second priority connection control part 170 becomes an L level and hence, the second switch part 140 is turned on. Further, an output signal of the first priority connection control part 160 becomes an H level and hence, the first switch part 130 is turned off. Accordingly, the power source is switched to the AC/DC power source connected to the second power source connector 104 from the battery power source connected to the first power source connector 102.

Further, an output signal of the first charge control part 162 becomes an L level and hence, the first charge control switch part 132 is turned on. Further, an output signal of the charge power source control part 180 becomes an L level and hence, an operation of the charge power source generation part 120 is turned on whereby a charge power source (16.8V) is generated from the AC/DC power source, and charging of the charge power source to the battery power source is started through the first charge control switch part 132. A supply voltage of the battery power source to which the supply of the charge power source is started is started to increase.

When a supply voltage of the battery power source connected to the first power source connector 102 becomes more than or equal to a charge completion voltage at a point of time T12 which comes after the point of time Ill, an output signal of the output terminal p2 of the first comparator CMP1 changes to an L level. Accordingly, an output signal of the first charge control part 162 changes to an H level and hence, the first charge control switch part 132 is turned off whereby the charging is stopped.

[Display of Switching of Power Sources]

In this embodiment, a connection state and a power source supply state of the power source connected to the power source switching part 100 are displayed on the display part 500 and hence, a patient does not feel anxiety about the sudden interruption of the supply of a power source thus enhancing reliability of the artificial heart system.

Figure 9:
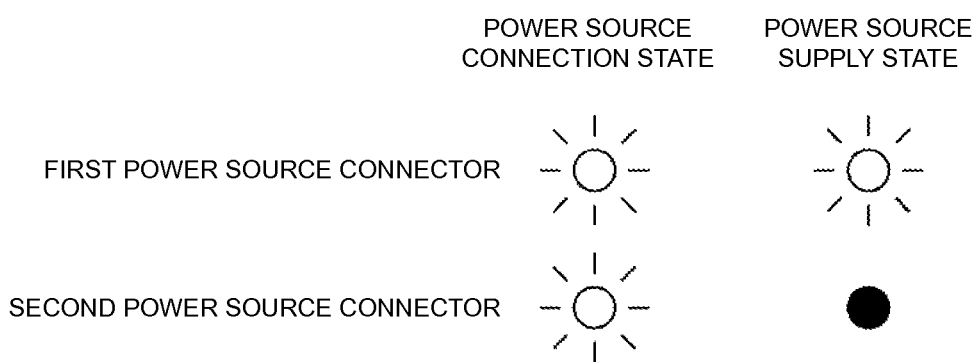
FIG. 9 is a view schematically showing a first display example of a display part according to the embodiment of the present invention.

FIG. 9 schematically shows a first display example of the display part 500 according to this embodiment. FIG. 9 shows the display example which displays that the battery power source or the AC/DC power source is connected to the first power source connector 102 and the second power source connector 104, and a power source is supplied to the load from the battery power source or the AC/DC power source connected to the first power source connector 102.

The control part 400 performs a display control of the display part 500 shown in FIG. 9 by monitoring internal signals in the power source switching part 100. In FIG. 9, a power source connection state is displayed in such a manner that a lighting display is performed corresponding to the power source connector to which the battery power source or the AC/DC power source is connected, and a non-lightening display is performed corresponding to the power source connector to which the battery power source or the AC/DC power source is not connected. Further, in FIG. 9, a power source supply state is displayed in such a manner that a lighting display is performed corresponding to the power source connector to which the power source by which a power source is supplied to the load is connected, and a non-lighting display is performed corresponding to the power source connector to which the power source by which a power source is not supplied to the load is connected.

The control part 400 determines whether or not the AC/DC power source is connected to the first power source connector 102 by monitoring the output terminal p1 of the first comparator CMP1, and can reflect the result of the determination on the display part 500.

The control part 400 also determines whether or not the battery power source which is connected to the first power source connector 102 is in a full charge state by monitoring the output terminal p2 of the first comparator CMP1, and can reflect the result of the determination on the display part 500.

The control part 400 also determines whether or not the battery power source which is connected to the first power source connector 102 is in a charge required state by monitoring the output terminal p3 of the first comparator CMP1, and can reflect the result of the determination on the display part 500.

The control part 400 also determines whether or not the battery power source which is connected to the first power source connector 102 is being charged by monitoring an output signal of the first charge control part 162, and can reflect the result of the determination on the display part 500.

The control part 400 also determines whether or not a power source is supplied to the load by the power source which is connected to the first power source connector 102 by monitoring an output signal of the first priority connection control part 160, and can reflect the result of the determination on the display part 500.

In the same manner, the control part 400 determines whether or not the AC/DC power source is connected to the second power source connector 104 by monitoring the output terminal p1 of the second comparator CMP2, and can reflect the result of the determination on the display part 500.

The control part 400 determines whether or not the battery power source which is connected to the second power source connector 104 is in a full charge state by monitoring the output terminal p2 of the second comparator CMP2, and can reflect the result of the determination on the display part 500.

The control part 400 also determines whether or not the battery power source which is connected to the second power source connector 104 is in a charge required state by monitoring the output terminal p3 of the second comparator CMP2, and can reflect the result of the determination on the display part 500.

The control part 400 also determines whether or not the battery power source which is connected to the second power source connector 104 is being charged by monitoring an output signal of the second charge control part 172, and can reflect the result of the determination on the display part 500.

The control part 400 also determines whether or not a power source is supplied to the load by the power source which is connected to the second power source connector 104 by monitoring an output signal of the second priority connection control part 170, and can reflect the result of the determination on the display part 500.

In FIG. 9, a lighting display or a non-lighting display may be performed separately between the battery power source and the AC/DC power source with respect to a power source connection state and a power source supply state.

FIG. 10 schematically shows a second display example of the display part 500 according to this embodiment. FIG. 10 shows a display example corresponding to a power source connection state and a power source supply state of the first power source connector 102 and the second power source connector 104. In FIG. 10, out of the power sources connected to the respective power source connectors, the power source which supplies a power source to the load is displayed in a surrounded manner by a frame in a left column.

In the example shown in FIG. 10, icons respectively corresponding to the battery power source and the AC/DC power source are prepared, and the display part 500 displays the icons corresponding to the power sources connected to the respective power source connectors. In this case, the icon corresponding to the battery power source includes: a plurality of residual capacity mark portions (in FIG. 10, rectangular marks) where the number of mark portions to be displayed is changed corresponding to a battery residual capacity; and a frame portion which surrounds the plurality of residual capacity mark portions.

When a power source is connected to each power source connector, the display part 500 displays the icon corresponding to the type of the power source determined by the control part 400.

When the battery power source is connected to the power source connector, the display part 500 displays the residual capacity mark portions the number of which corresponds to a battery residual capacity. For example, a battery residual capacity is reflected on the display part 500 such that the first comparator CMP1 and the second comparator CMP2 are made to output the result of the comparison between a detection voltage corresponding to a residual capacity and a voltage of each power source connector respectively and the control part 400 detects the results of the comparisons and reflect the battery residual capacity based on the results of the comparisons. Further, when a power source is supplied to the load from the battery power source, the display part 500 displays also the frame portion in addition to the residual capacity mark portions.

As descried above, the display part 500 displays a power source connection state and a power source supply state of a power source connected to the power source switching part 100 and hence, it is possible to eliminate anxiety which a patient who mounts the artificial heart system may have thus further enhancing reliability of the equipment.

[Modification]

In the power source switching part 100 of this embodiment, the explanation has been made with respect to the example where the function of the switching control part 150 is realized using a logic circuit. This embodiment, however, is not limited to such an example.

Figure 11:
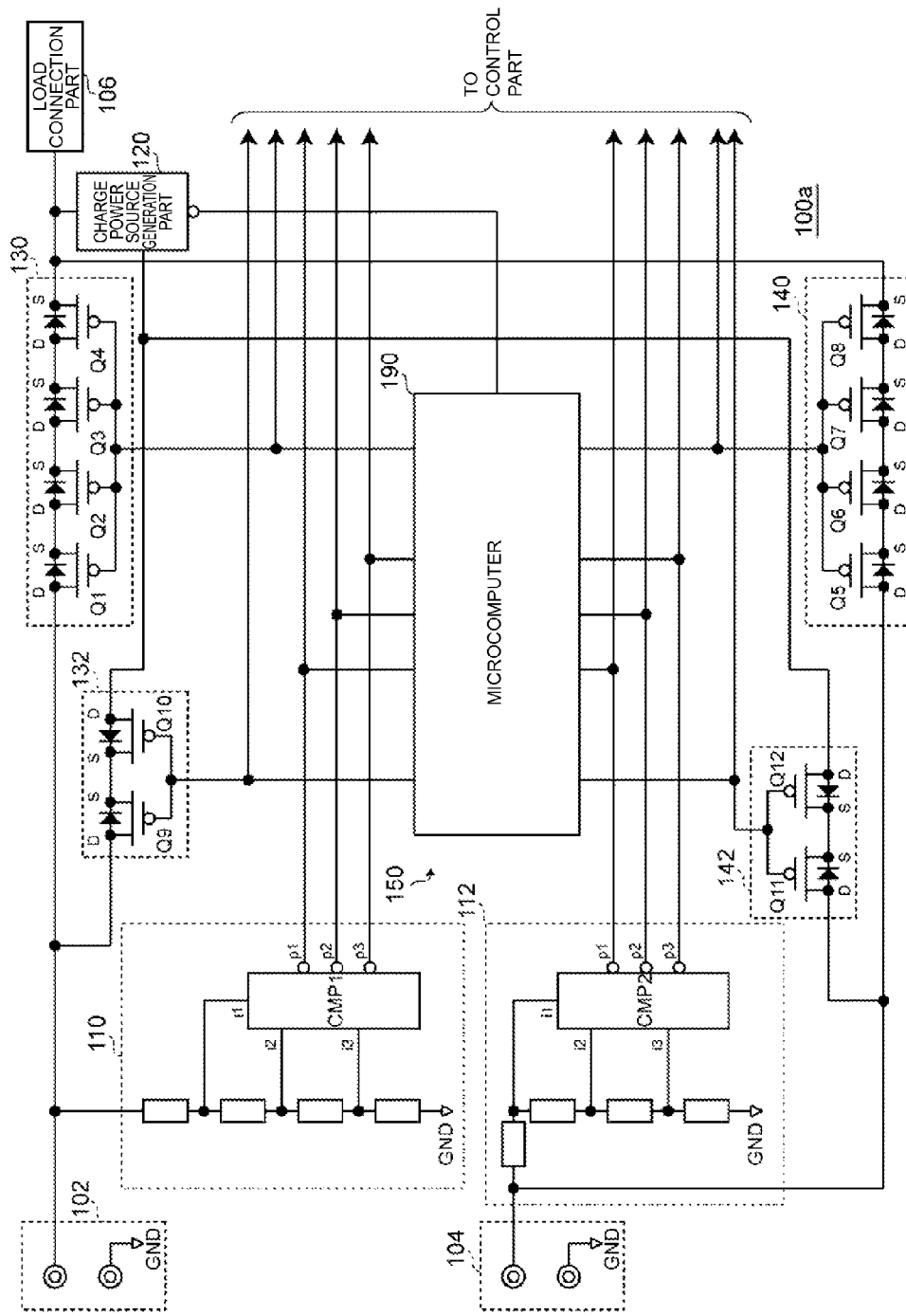
FIG. 11 is a circuit diagram of a constitutional example of a power source switching part according to a modification of the embodiment of the present invention.

FIG. 11 is a circuit diagram showing a constitutional example of a power source switching part according to a modification of this embodiment. In FIG. 11, constitutional parts substantially equal to the corresponding constitutional parts shown in FIG. 3 are given the same symbols and the explanation of these constitutional parts is omitted when appropriate. A power source switching part shown in FIG. 11 is applicable to the artificial heart control device shown in FIG. 1 in place of the power source switching part 100.

The constitution of a power source switching part 100a according to this modification differs from the constitution of the power source switching part 100 shown in FIG. 3 with respect to a point that the logic circuit which constitutes the switching control part 150 shown in FIG. 3 is replaced with a microcomputer 190. That is, functions of the arrival order holding part 152, the first priority connection control part 160, the first charge control part 162, the second priority connection control part 170, the second charge control part 172, and the charge power source control part 180 shown in FIG. 3 are realized by the microcomputer 190 in this modification.

The microcomputer includes: a central processing unit (hereinafter referred to as CPU); a memory; and a plurality of I/O ports. The CPU reads a program preliminarily stored in the memory and executes processing corresponding to the program. The I/O ports are connected to output terminals p1 to p3 of a first comparator CMP1 and a second comparator CMP2, gates of FETs which respectively constitute a first switch part 130, a second switch part 140, a first charge control switch part 132 and a second charge control switch part 142, and a control terminal of a charge power source generation part 120.

The CPU controls the gates of the FETs constituting the first switch part 130, the second switch part 140, the first charge control switch part 132 and the second charge control switch part 142 which are connected to the I/O ports, and control terminals of a charge power source generation part 120 which are connected to the I/O ports based on states of the output terminals p1 to p3 of the respective comparators which are inputted to the CPU through the I/O ports.

In FIG. 11, the microcomputer 190 may be configured to incorporate at least one function out of functions which the first power source detection part 110, the second power source detection part 112, the first switch part 130, the second switch part 140, the first charge control switch part 132, the second charge control switch part 142, and the charge power source generation part 120 respectively have.

According to this modification, it is possible to acquire the substantially same advantageous effects as the above-mentioned embodiment with the small number of elements.

The power source switching circuit, the artificial heart system and the like according to the present invention have been explained in conjunction with the above-mentioned embodiment and the modification of the embodiment heretofore. However, the present invention is not limited to the above-mentioned embodiment and the modification of the embodiment, and can be carried out in various modes without departing from the gist of the present invention. For example, the following modifications are also conceivable.

(1) In the above-mentioned embodiment and the modification of the embodiment, the explanation has been made with respect to the case where the power source switching circuit performs the switching of the power sources of two systems. However, the switching of power sources of three or more systems may be performed.

(2) In the above-mentioned embodiment and the modification of the embodiment, the explanation has been made with respect to the case where p-type FETs are adopted as the FETs which constitute the first switch part and the second switch part. However, the present invention is not limited to such a case. For example, provided that the direction of terminals of body diodes are equal to the direction of terminals of the body diodes employed in the above-mentioned embodiment and the modification of the embodiment, the first switch part and the second switch part may be constituted of n-type FETs.

(3) In the above-mentioned embodiment and the modification of the embodiment, the explanation has been made with respect to the case where the blood pump is a continuous flow type pump. However, the present invention is not limited to such a case, and the blood pump may be a pulsation flow type blood pump which imparts a predetermined cycle to the flow of blood to be circulated or a magnetic levitation blood pump.

(4) The blood pump according to the above-mentioned embodiment and the modification of the embodiment is realized by an AC motor driven by drive signals of three phases, a motor driven by a drive signal other than drive signals of three phases or a DC motor, for example.

(5) In the above-mentioned embodiment and the modification of the embodiment, the explanation has been made by taking the artificial heart system as an example of electric equipment. However, the present invention is not limited to the artificial heart system, and the present invention is also applicable to various other electric equipment.

(6) In the above-mentioned embodiment and the modification of the embodiment, the explanation has been made with respect to the case where the present invention is directed to the power source switching circuit, the artificial heart system and the like. However, the present invention is not limited to these objects. For example, the present invention may be directed to a program in which processing steps of a method of controlling the power source switching circuit according to the present invention is described, a program in which a processing steps of a display method of the display part 500 by the control part 400 is described, or a recording medium in which the program is recorded.

Explanation Of Symbols

10: artificial heart system, 20: artificial heart control device, 30: blood pump, 50: heart, 100, 100a: power source switch part (power source switching circuit), 102: first power source connector (first power source connection part), 104: second power source connector (second power source connection part), 106: load connection part, 110: first power source detection part, 112: second power source detection part: 120: charge power source generation part 130: first switch part, 132: first charge control switch part, 140: second switch part, 142: second charge control switch part, 150: switching control part, 152: arrival order holding part, 160: first priority connection control part, 162: first charge control part, 170: second priority connection control part, 172: second charge control part, 180: charge power source control part, 190: microcomputer, 200: power source generation part, 300: blood pump control part, 400: control part, 500: display part, CMP1: first comparator, CMP2: second comparator

The invention claimed is:

1. A power source switching circuit for selectively connecting a first power source and a second power source where at least one of the first and second power sources is a battery power source to a load by switching the first power source and the second power source, the power source switching circuit comprising:
   a first power source connection part configured to enable the connection of the first power source thereto;
   a second power source connection part configured to enable the connection of the second power source thereto;
   a load connection part configured to enable the connection of the load thereto;
   a first switch part provided between the first power source connection part and the load connection part;
   a second switch part provided between the second power source connection part and the load connection part; and
   a switching control part configured to perform a switch control of the first switch part and the second switch part,
   wherein each one of the first switch part and the second switch part includes
   a plurality of field effect transistors which are serially connected in the same direction such that a cathode side of a body diode of each field effect transistor is arranged on a load connection part side, and are subjected to the switch control performed by the switching control part, and
   the number of plurality of field effect transistors is the number determined such that a sum of forward drop voltages of the plurality of serially connected body diodes exceeds the difference between a full charge voltage and a discharge voltage of the battery power source.

2. The power source switching circuit according to claim 1, wherein the second power source connection part is configured to enable the connection of a third power source which is an AC/DC power source thereto, and
   the switching control part performs the switch control of the first switch part and the second switch part such that the power source is switched to the third power source from the first power source so as to supply a power source to the load when the third power source is connected to the second power source connection part in a state where the first power source connected to the first power source connection part supplies power source to the load.

3. The power source switching circuit according to claim 2 further comprising:
   a second power source detection part which detects a supply voltage of the power source connected to the second power source connection part, and
   the switching control part performs a switch control of the first switch part and the second switch part such that the power source is switched to the third power source from the first power source so as to supply a power source to the load when the connection of the third power source to the second power source connection part is detected based on a detection result of the second power source detection part.

4. The power source switching circuit according to claim 3, wherein the second power source detection part compares a supply voltage of the third power source and an AC/DC power source detection level with each other, and detects the connection of the third power source when the supply voltage of the third power source is higher than or equal to the AC/DC power source detection level.

5. The power source switching circuit according to claim 3 further comprising:
   a charge power source generation part which generates charge power source based on a voltage supplied to the load connection part; and
   a first charge control switch part provided between the charge power source generation part and the first power source connection part, wherein
   the switching control part performs the switch control of the first charge control switch part so as to supply the charge power source to the first power source connection part when the switching control part detects the connection of the third power source to the second power source connection part.

6. The power source switching circuit according to claim 5 further comprising:
   a first power source detection part which detects a voltage of the first power source connection part, wherein
   the switching control part performs a switch control of the first charge control switch part so as to stop the supply of the charge power source to the first power source connection part when a supply voltage of the power source connected to the first power source connection part is higher or equal to a charge completion voltage which is higher than the full charge voltage.

7. The power source switching circuit according to claim 5 further comprising: a second charge control switch part provided between the charge power source generation part and the second power source connection part, wherein
   the switching control part performs a switch control of the second charge control switch part so as to supply the charge power source to the second power source connection part when the switching control part detects the connection of the third power source to the first power source connection part.

8. The power source switching circuit according to claim 7, wherein the switching control part performs a switch control of the second charge control switch part so as to stop the supply of the charge power source to the second power source connection part when a voltage of the second power source connection part is higher or equal to a charge completion voltage which is higher than the full charge voltage.

9. The power source switching circuit according to claim 1, wherein the switching control part is configured to continue the supply of a power source to the load by the first power source when the second power source is connected to the second power source connection part in a state where the first power source connected to the first power source connection part supplies power source to the load.

10. The power source switching circuit according to claim 9, wherein the switching control part is configured to perform a switch control of the first switch part and the second switch part so as to supply a power source to the load by switching the power source to the second power source from the first power source when a supply voltage from the first power source becomes less than the discharge voltage.

* * * * *